(12) United States Patent
Slayton et al.

(10) Patent No.: US 12,194,320 B2
(45) Date of Patent: Jan. 14, 2025

(54) SYSTEMS AND METHODS FOR IMPROVING AN OUTSIDE APPEARANCE OF SKIN USING ULTRASOUND AS AN ENERGY SOURCE

(71) Applicant: Guided Therapy Systems, LLC, Scottsdale, AZ (US)

(72) Inventors: Michael H. Slayton, Phoenix, AZ (US); Peter G. Barthe, Phoenix, AZ (US)

(73) Assignee: Guided Therapy Systems, LLC, Scottsdale, AZ (US)

( * ) Notice: Subject to any disclaimer, the term of this patent is extended or adjusted under 35 U.S.C. 154(b) by 0 days.

(21) Appl. No.: 18/371,925

(22) Filed: Sep. 22, 2023

(65) Prior Publication Data

US 2024/0269490 A1    Aug. 15, 2024

Related U.S. Application Data

(63) Continuation of application No. 14/868,947, filed on Sep. 29, 2015, now abandoned, which is a continuation-in-part of application No. 13/545,954, filed on Jul. 10, 2012, now abandoned.

(60) Provisional application No. 61/506,610, filed on Jul. 11, 2011, provisional application No. 61/506,609, filed on Jul. 11, 2011, provisional application No. 61/506,126, filed on Jul. 10, 2011, provisional application No. 61/506,125, filed on Jul. 10, 2011, (Continued)

(51) Int. Cl.
*A61N 7/02*    (2006.01)
*A61B 8/00*    (2006.01)
*A61B 8/08*    (2006.01)
*A61B 18/00*   (2006.01)
*A61B 18/20*   (2006.01)
*A61H 23/02*   (2006.01)
*A61N 5/06*    (2006.01)
*A61N 7/00*    (2006.01)

(52) U.S. Cl.
CPC .............. *A61N 7/02* (2013.01); *A61B 18/203* (2013.01); *A61H 23/0245* (2013.01); *A61N 5/0616* (2013.01); *A61B 8/4472* (2013.01); *A61B 8/483* (2013.01); *A61B 2018/00452* (2013.01); *A61H 2201/5007* (2013.01); *A61N 7/00* (2013.01); *A61N 2007/0008* (2013.01); *A61N 2007/0034* (2013.01); *A61N 2007/0073* (2013.01); *A61N 2007/0078* (2013.01); *A61N 2007/027* (2013.01)

(58) Field of Classification Search
CPC ........ A61B 2018/00476; A61B 18/203; A61B 18/20; A61B 2018/00452; A61N 7/02
See application file for complete search history.

*Primary Examiner* — Ashley K Buran
*Assistant Examiner* — Helene Bor
(74) *Attorney, Agent, or Firm* — GTC Law Group

(57) ABSTRACT

In some embodiments, the method can comprise locating a targeted portion of skin surface; delivering ultrasound energy to subcutaneous tissue below the skin surface; producing a biological effect in at least one of the skin surface and the subcutaneous tissue; and improving the appearance of the targeted portion of the skin surface. Improving the appearance of the skin surface can be at least one of increasing skin elasticity, reducing skin oiliness, reducing skin pore size, smoothing skin texture, reducing hyperpigmentation, treating and/or preventing acne, reducing a blemish, reducing an appearance of spider veins and/or rosacea, reducing an appearance of scars, reducing an appearance of stretch marks, rejuvenating skin, increasing collagen in the subcutaneous tissue, tightening of sagging sink, rejuvenating photoaged skin, increasing a thickness of a dermal layer, reducing a wrinkle on the skin surface, generating new tissue in the subcutaneous layer, and combinations thereof.

12 Claims, 8 Drawing Sheets

Related U.S. Application Data provisional application No. 61/506,127, filed on Jul. 10, 2011, provisional application No. 61/506,160, filed on Jul. 10, 2011, provisional application No. 61/506,163, filed on Jul. 10, 2011.

SYSTEMS AND METHODS FOR IMPROVING AN OUTSIDE APPEARANCE OF SKIN USING ULTRASOUND AS AN ENERGY SOURCE

CROSS-REFERENCE TO RELATED APPLICATIONS

This application is a continuation of and claims priority to U.S. patent application Ser. No. 14/868,947 filed Sep. 29, 2015, Publication No. US 2016-0016015 A1, and entitled "Systems and Methods for Improving an Outside Appearance of Skin Using Ultrasound as an Energy Source" (2080.0013).

U.S. application Ser. No. 14/868,947 claims priority to, and is a continuation-in-part of Ser. No. 13/545,954 filed Jul. 10, 2012, now abandoned, and entitled "Systems and Methods for Improving an Outside Appearance of Skin Using Ultrasound as an Energy Source" (2080.0048).

U.S. application Ser. No. 13/545,954 claims priority to and the benefit of U.S. Provisional Patent Application Ser. No. 61/506,125 filed Jul. 10, 2011, and entitled "Systems and Methods for Creating Shaped Lesions" (2080.0024); U.S. Provisional Patent Application Ser. No. 61/506,127 filed Jul. 10, 2011, and entitled "Systems and Methods for Treating Injuries to Joints and Connective Tissue" (2080.0026); U.S. Provisional Patent Application Ser. No. 61/506,126 filed Jul. 10, 2011, and entitled "System and Methods for Accelerating Healing of Implanted Materials and/or Native Tissue" (2080.0025); U.S. Provisional Patent Application Ser. No. 61/506,160 filed Jul. 10, 2011, and entitled "Systems and Methods for Cosmetic Rejuvenation" (2080.0027); U.S. Provisional Patent Application Ser. No. 61/506,163 filed Jul. 10, 2011, and entitled "Methods and Systems for Ultrasound Treatment" (2080.0028); U.S. Provisional Patent Application Ser. No. 61/506,609 filed Jul. 11, 2011, and entitled "Systems and Methods for Monitoring Ultrasound Power Efficiency" (2080.0029); and U.S. Provisional Patent Application Ser. No. 61/506,610 filed Jul. 11, 2011, and entitled "Methods and Systems for Controlling Acoustic Energy Deposition into a Medium" (2080.0030); all of which are incorporated by reference herein.

BACKGROUND

Energy, such as ultrasound energy, can be applied to treat tissue or perform traditionally invasive procedures in a non-invasive manner. The application of ultrasound energy provides both thermal and/or mechanical effects that help treat certain ailments such as acne and enable many traditional invasive procedures to be performed non-invasively.

Typically, ultrasound devices only affect, a specific portion of the tissue at a certain depth within the region of interest based upon the configuration of the particular ultrasound device. For example, an ultrasound device might be configured to affect an area five millimeters below the surface of the skin. The tissue from the surface of the skin to the depth of five millimeters is spared and not treated by the ultrasound energy. Sparing these intervening spaces of tissue hinders the overall beneficial effect of ultrasound as treatment of this intervening tissue increases ultrasound treatment's overall efficacy. Accordingly, new approaches of cosmetic enhancement of skin are needed, which are rapid and non-invasive.

SUMMARY

Various embodiments described herein provide methods and systems for cosmetic enhancement of tissue. Accordingly, ultrasound energy can be focused, unfocused or defocused and can be applied to a region of interest containing subcutaneous tissue below a surface to achieve a cosmetic effect.

Various embodiments provide a method for improving an appearance of a skin surface. In some embodiments, the method can comprise locating a targeted portion of skin surface; delivering ultrasound energy to subcutaneous tissue below the skin surface; producing a biological effect in at least one of the skin surface and the subcutaneous tissue; and improving the appearance of the targeted portion of the skin surface.

In some embodiments, the improving the appearance of the targeted portion of the skin surface comprises at least one of increasing skin elasticity, reducing skin oiliness, reducing skin pore size, smoothing skin texture, reducing hyperpigmentation, treating and/or preventing acne, reducing a blemish, reducing an appearance of spider veins and/or rosacea, reducing an appearance of scars, reducing an appearance of stretch marks, rejuvenating skin, increasing collagen in the subcutaneous tissue, tightening of sagging skin, rejuvenating photoaged skin, increasing a thickness of a dermal layer, reducing a wrinkle on the skin surface, generating new tissue in the subcutaneous layer, and combinations thereof.

Various embodiments provide a method for improving an appearance of a skin surface. In some embodiments, the method can comprise locating a targeted portion of skin surface; delivering ultrasound energy to subcutaneous tissue below the skin surface; producing a biological effect in at least one of the skin surface and the subcutaneous tissue; and improving the appearance of the targeted portion of the skin surface.

Various embodiments provide a system for improving the appearance of a skin surface. In some embodiments, the system can further comprise a hand-held probe comprising: an ultrasound transducer; an indicator display; at least one input/output control; a position sensor; and a rechargeable battery configured to power the handheld probe. In some embodiments, the system can further comprise a controller configured to control the hand-held probe; and a wireless interface configured to couple communication between the controller and the hand-held probe.

In some embodiments, the controller is at least one of a personal data assistant, a cell phone, an iPhone, an iPad, a computer, a laptop, and a netbook. In some embodiments, the transducer is configured as a 2 dimensional linear array.

DRAWINGS

The present disclosure will become more fully understood from the detailed description and the accompanying drawings, wherein.

Figure 10A:
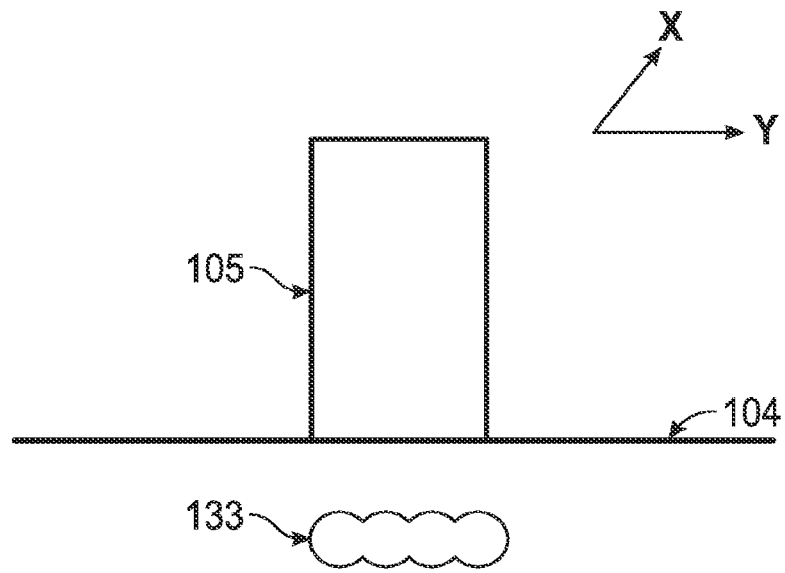
Figure 10B:
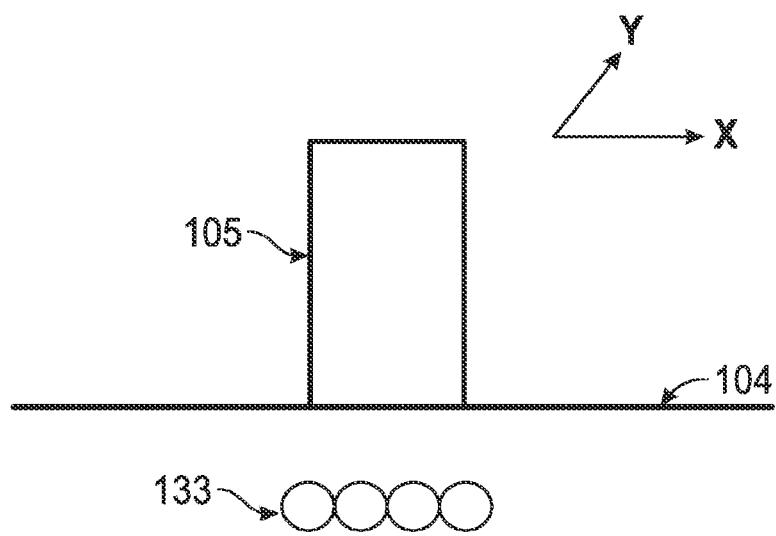
Figure 11A:
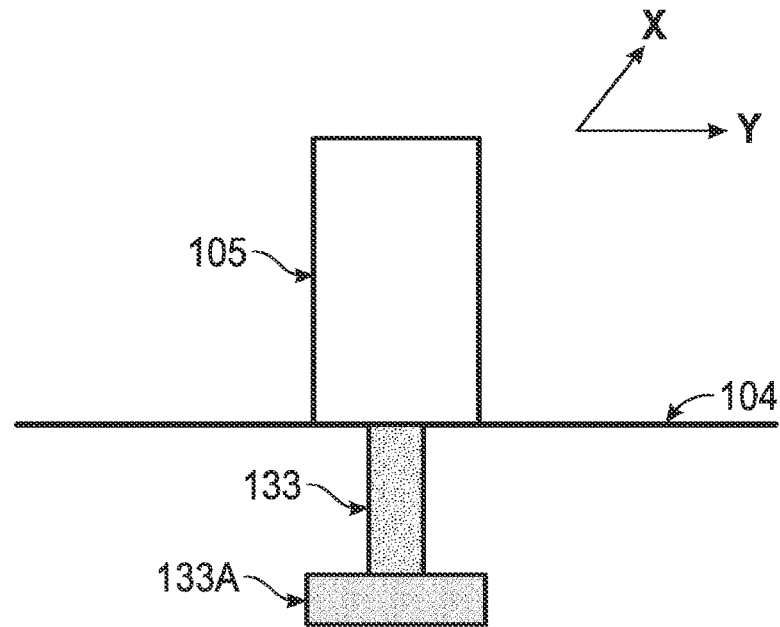
Figure 11B:
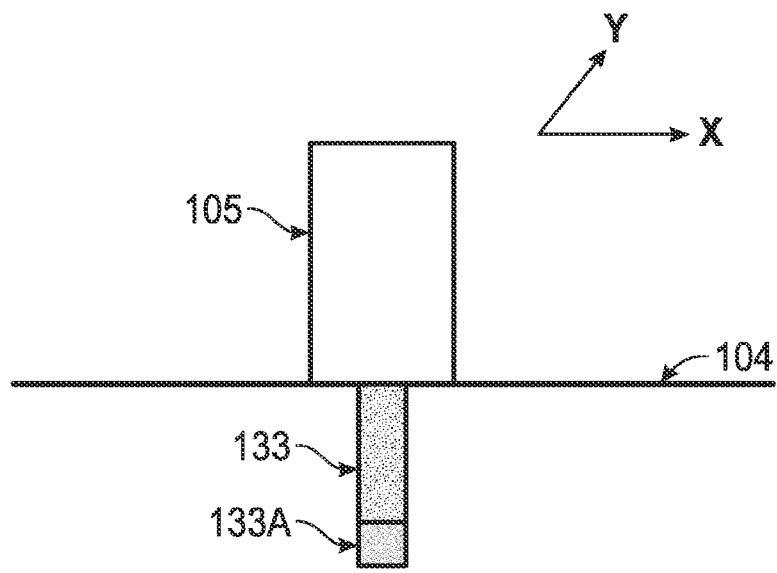
Figure 12:
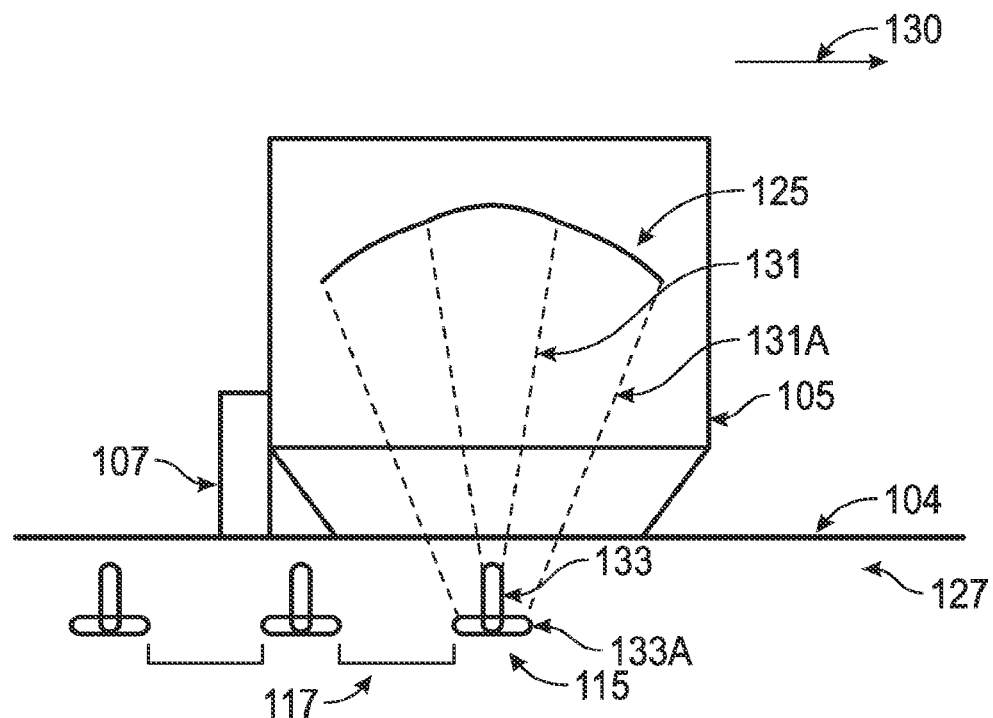
Figure 13:
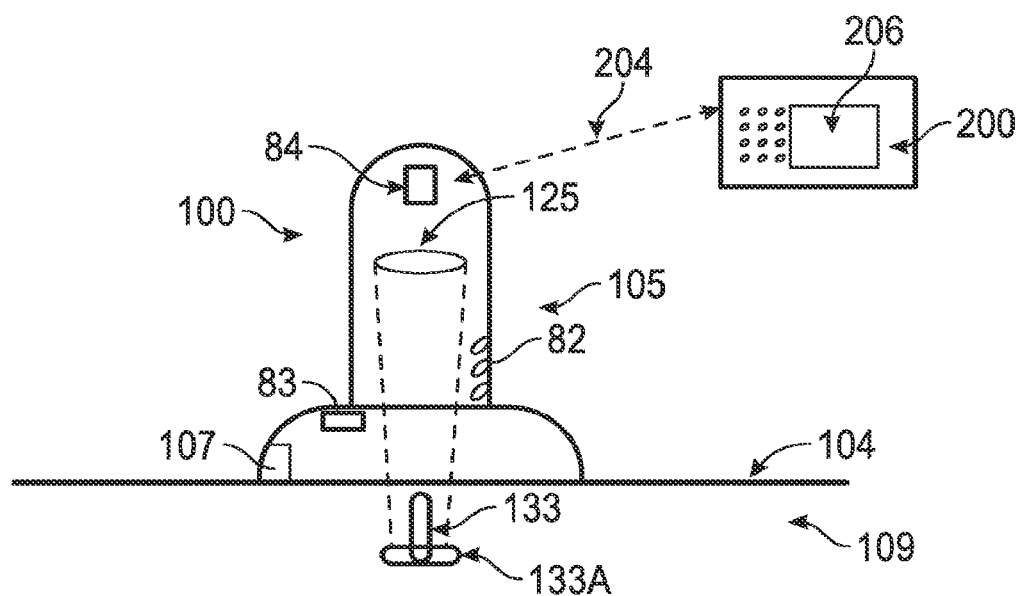

FIGS. 10 A-B are a cross sectional views illustrating conformal region of elevated temperature and second conformal region of elevated temperature in soft tissue, according to various non-limiting embodiments;

FIGS. 11 A-B are a cross sectional views illustrating conformal region of elevated temperature and second conformal region of elevated temperature in soft tissue, according to various non-limiting embodiments;

FIG. 12 is a cross sectional view illustrating a plurality of conformal region of elevated temperature and second conformal region of elevated temperature m subcutaneous tissue, according to various non-limiting embodiments; and FIG. 13 is a cross sectional view illustrating a hand held probe, according to various non-limiting embodiments,

DESCRIPTION

The following description is merely exemplary in nature and is in no way intended to limit the various embodiments, their application, or uses. As used herein, the phrase "at least one of A, B, and C" should be construed to mean a logical (A or B or C), using a non-exclusive logical "or." As used herein, the phrase "A, B and/or C" should be construed to mean (A, B, and C) or alternatively (A or B or C), using a non-exclusive logical "or." It should be understood that steps within a method may be executed in different order without altering the principles of the present disclosure.

The drawings described herein are for illustrative purposes only of selected embodiments and not all possible implementations, and are not intended to limit the scope of any of the various embodiments disclosed herein or any equivalents thereof. It is understood that the drawings are not drawn to scale. For purposes of clarity, the same reference numbers will be used in the drawings to identify similar elements.

The various embodiments may be described herein in terms of various functional components and processing steps. It should be appreciated that such components and steps may be realized by any number of hardware components configured to perform the specified functions. For example, various embodiments may employ various medical treatment devices, visual imaging and display devices, input terminals and the like, which may carry out a variety of functions under the control of one or more control systems or other control devices. In addition, the embodiments may be practiced in any number of medical contexts and that the various embodiments relating to a method and system for acoustic tissue treatment as described herein are merely indicative of exemplary applications for the invention. For example, the principles, features and methods discussed may be applied to any medical application. Further, various aspects of the various embodiments may be suitably applied to cosmetic applications. Moreover, some of the embodiments may be applied to cosmetic enhancement of skin and/or various subcutaneous tissue layers.

According to various embodiments, methods and systems useful for cosmetic rejuvenation of face and body are provided herein. The methods and systems provided herein are noninvasive, for example, no cutting or injecting into the skin is required. Cosmetic rejuvenation of the face and/or body using the methods and systems provided herein minimize recover time and may in some cases eliminate downtime for recovery. Further cosmetic rejuvenation using the methods and systems provided herein minimize discomfort to a patient having such a rejuvenation procedure.

Various embodiments provide a hand-held extracorporeal apparatus, which emits controlled ultrasound energy into layers of the skin to create a conformal region of elevated temperature in tissue of the skin. In some embodiments, a system useful for cosmetic rejuvenation of the face and/or body is in a handheld format which may include a rechargeable power supply.

In various embodiments, rejuvenation is a reversal or an attempt to reverse the aging process. Rejuvenation can be the reversal of aging and is namely repair of the damage that is associated with aging or replacement of damaged tissue with new tissue. In some embodiments, cosmetic enhancement can refer to procedures, which may not be medically necessary but can be used to improve or change the appearance of a portion of the body. For example, a cosmetic enhancement can be a procedure but not limited to procedures that are used to improve or change the appearance of a nose, eyes, eyebrows and/or other facial features, or to improve or change the appearance and/or the texture and/or the elasticity of skin, or to improve or change the appearance of a mark or scar on a skin surface, or to improve or change the appearance and/or the content of fat near a skin surface, or the targeting of a gland to improve or change the appearance a portion of the body. In at least some embodiments, cosmetic enhancement is a non-surgical and non-invasive procedure. In various embodiments, cosmetic enhancement provides rejuvenation to at least one portion of the body.

In some embodiments, methods of cosmetic enhancement can increase elasticity of skin by thinning a dermis layer, thereby rejuvenating a portion of skin. In some embodiments, methods of cosmetic enhancement can stimulate initiation of internal body resources for the purpose of repairing an injury and/or cell deficiency.

Various embodiments provide a method for improving an appearance of a skin surface. In some embodiments, the method can comprise locating a targeted portion of skin surface; targeting a region of interest comprising the targeted portion of the skin surface and subcutaneous tissue below the skin surface; delivering ultrasound energy to the region of interest; producing an effect in at least one of the skin surface and the subcutaneous tissue; and improving the appearance of the targeted portion of the skin surface.

In some embodiments, the method can further comprise imaging the subcutaneous tissue below the skin surface. In some embodiments, the method can further comprise administering a medicant to the region of interest. In some embodiments, the method can further comprise activating the medicant in the region of interest with the ultrasound energy at the same frequency or a different frequency.

In some embodiments, the method can further comprise delivering a secondary energy to the region of interest. In some embodiments, the secondary energy is a photon-based energy. In some embodiments, the secondary energy is radio frequency based energy. In some embodiments, the method can further comprise determining results of the effect in at least one of the skin surface and the subcutaneous tissue.

In some embodiments, the effect is a cosmetic effect. In some embodiments, the cosmetic effect is at least one of increasing skin elasticity/tighten skin, reducing skin oiliness, reducing skin pore size, smoothing skin texture, reducing hyperpigmentation, reducing fat, reducing cellulite, treating and/or preventing acne, treating hyperhidrosis, reducing an appearance of spider veins and/or rosacea, reducing an appearance of scars, reducing an appearance of stretch marks, treating of soft tissue in the region of interest, rejuvenating skin, increasing skin elasticity, increasing collagen in tissue, smoothing of the texture of skin, tightening of sagging sink, rejuvenating photoaged skin, increasing a thickness of a dermal layer, reducing a wrinkle on the skin surface, lifting of skin, body sculpting, generating new tissue in the subcutaneous tissue, and combinations thereof.

In some embodiments, the improving the appearance of the targeted portion of the skin surface comprises at least one of increasing skin elasticity, reducing skin oiliness, reducing skin pore size, smoothing skin texture, reducing hyperpigmentation, treating and/or preventing acne, reducing a blemish, reducing an appearance of spider veins and/or rosacea, reducing an appearance of scars, reducing an appearance of stretch marks, rejuvenating skin, increasing collagen in the subcutaneous tissue, tightening of sagging skin, rejuvenating photoaged skin, increasing a thickness of a dermal layer, reducing a wrinkle on the skin surface, generating new tissue in the subcutaneous layer, and combinations thereof.

Various embodiments provide a method for improving an appearance of a skin surface. In some embodiments, the method can comprise locating a targeted portion of skin surface; delivering ultrasound energy to subcutaneous tissue below the skin surface; producing a biological effect in at least one of the skin surface and the subcutaneous tissue; and improving the appearance of the targeted portion of the skin surface.

In some embodiments, the method can further comprise delivering a medicant to the subcutaneous tissue below the skin surface. In some embodiments, the method can further comprise comprising activating the medicant in the region of interest with the ultrasound energy at the same frequency or a different frequency. In some embodiments, the method can further comprise delivering a cosmeceutical to the subcutaneous tissue below the skin surface.

In some embodiments, the method can further comprise delivering a secondary energy to the subcutaneous tissue below the skin surface. In some embodiments, the secondary energy is a photon-based energy. In some embodiments, the secondary energy is radio frequency based energy.

In some embodiments, the biological effect is at least one of stimulating or increase an amount of heat shock proteins, cause white blood cells to promote healing of a portion of the subcutaneous tissue, accelerating to wound healing cascade in the subcutaneous tissue, increasing the blood perfusion in the subcutaneous tissue, encouraging collagen growth in the subcutaneous tissue, increasing the liberation of cytokines within the subcutaneous layer, peaking inflammation in the subcutaneous tissue, partially shrinking collagen in a portion of the subcutaneous tissue, denaturing of proteins in the subcutaneous tissue, and combinations thereof.

In some embodiments, the biological effect is at least one of creating immediate or delayed cell death in the subcutaneous tissue, collagen remodeling in the subcutaneous tissue, disrupting or modifying of biochemical cascades in at least one of the skin surface and the subcutaneous tissue, producing new collagen in the subcutaneous tissue, stimulating cell growth in the subcutaneous tissue, stimulating angiogenesis, stimulating a cell permeability response, enhancing delivery of medicants into the subcutaneous tissue, and combinations thereof.

In some embodiments, the improving the appearance of the targeted portion of the skin surface comprises at least one of increasing skin elasticity, reducing skin oiliness, reducing skin pore size, smoothing skin texture, reducing hyperpigmentation, treating and/or preventing acne, reducing a blemish, reducing an appearance of spider veins and/or rosacea, reducing an appearance of scars, reducing an appearance of stretch marks, rejuvenating skin, increasing collagen in the subcutaneous tissue, tightening of sagging skin, rejuvenating photoaged skin, increasing a thickness of a dermal layer, reducing a wrinkle on the skin surface, generating new tissue in the subcutaneous layer, and combinations thereof.

Various embodiments provide a system for improving the appearance of a skin surface. In some embodiments, the system can further comprise a hand-held probe comprising: an ultrasound transducer; an indicator display; at least one input/output control; a position sensor; and a rechargeable battery configured to power the handheld probe. In some embodiments, the system can further comprise a controller configured to control the hand-held probe and a wireless interface configured to couple communication between the controller and the hand-held probe.

In some embodiments, the controller is at least one of a personal data assistant, a cell phone, an iPhone, an iPad, a computer, a laptop, and a netbook. In some embodiments, the transducer is configured as a 2 dimensional linear array.

In various embodiments, the system and the related method of the present invention apply ultrasound energy to a region of interest at the surface of the patient's skin and ultrasound energy travels from the surface to a location within the region of interest and treats all the tissue within the region of interest with a combined energy profile without sparing any of such tissue.

In some embodiments, the ultrasound transducer is configured to simultaneously create a first conformal region of elevated temperature and second conformal region of elevated temperature in subcutaneous tissue. In some embodiment, the first conformal region of elevated temperature and second conformal region of elevated temperature intersect in the subcutaneous tissue. In some embodiments, the first conformal region of elevated temperature and second conformal region of elevated temperature are positioned perpendicular to each other in the subcutaneous tissue.

Various embodiments provide a method for treating a surface of skin. In some embodiments, the method can comprise creating a conformal region of elevated temperature; treating a surface and subsurface of skin simultaneously; creating a transitional biological effect on the surface of the skin without causing cell death, a scar, or permanent damage to the surface of the skin; creating a thermal effect to the subsurface of the skin; and initiating a permanent biological effect to the subsurface of the skin. The method can further comprise creating an optically-visible effect on the surface of the skin. The transitional biological effect can be one of erythema, edema, and a transitional coagulative point. In some embodiments, the optically visible effect on the surface of the skin can be at least one of at least one of increasing skin elasticity, reducing skin oiliness, reducing skin pore size, smoothing skin texture, reducing hyperpigmentation, treating and/or preventing acne, reducing a blemish, reducing an appearance of spider veins and/or rosacea, reducing an appearance of scars, reducing an appearance of stretch marks, rejuvenating skin, increasing collagen in the subcutaneous tissue, tightening of sagging skin, rejuvenating photoaged skin, increasing a thickness of a dermal layer, reducing a wrinkle on the skin surface, generating new tissue in the subcutaneous layer, and combinations thereof.

In some embodiments, the permanent biological effect can be at least one of stimulating or increase an amount of heat shock proteins, cause white blood cells to promote healing of a portion of the subcutaneous tissue, accelerating to wound healing cascade in the subcutaneous tissue, increasing the blood perfusion in the subcutaneous tissue, encouraging collagen growth in the subcutaneous tissue, increasing the liberation of cytokines within the subcutaneous layer, peaking inflammation in the subcutaneous tissue, partially shrinking collagen in a portion of the subcutaneous tissue, denaturing of proteins in the subcutaneous tissue, and combinations thereof.

In some embodiments, the permanent biological effect is at least one of creating immediate or delayed cell death in the subcutaneous tissue, collagen remodeling in the subcutaneous tissue, disrupting or modifying of biochemical cascades in at least one of the skin surface and the subcutaneous tissue, producing new collagen in the subcutaneous tissue, stimulating cell growth in the subcutaneous tissue, stimulating angiogenesis, stimulating a cell permeability response, enhancing delivery of medicants to in the subcutaneous tissue, and combinations thereof.

Figure 1:
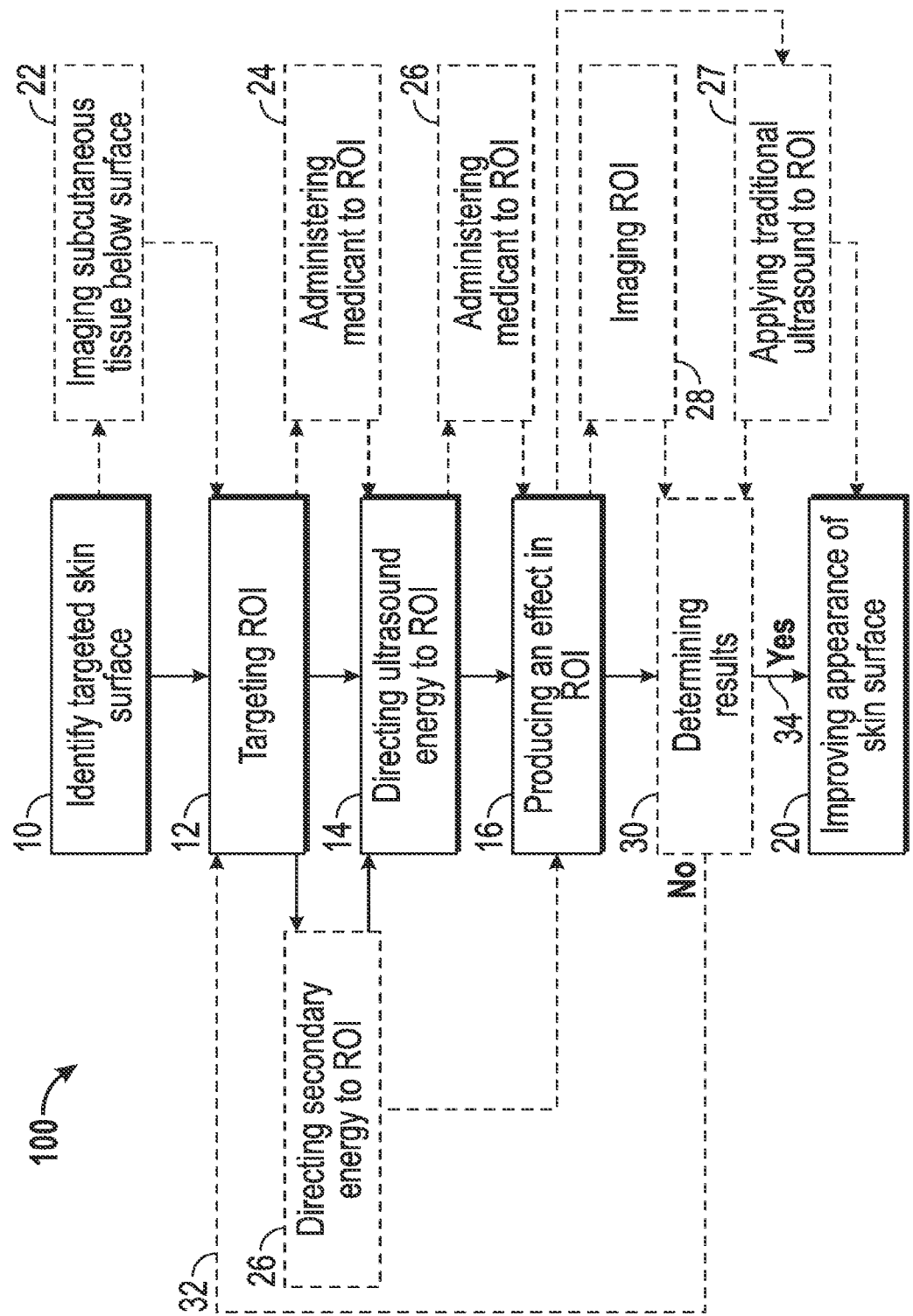
FIG. 1 is a flow chart illustrating methods of cosmetic enhancement, according to various non-limiting embodiments.

With reference to FIG. 1, a method of cosmetic enhancement 100 is illustrated according to various embodiments. Step 10 is identifying a targeted skin surface, which may be located anywhere on the body, such as, for example, in any of the following: face, neck, hands, arms, legs, buttocks, and combinations thereof. Next, Step 12 is targeting a region of interest ("ROI"). The ROI can be located in subcutaneous tissue below the targeted skin surface, which can be anywhere in the body, such as, those listed previously. The subcutaneous tissue can comprise any or all of the following tissues: an epidermal layer, a dermal layer, a fat layer, a SMAS layer, and a muscle layer. Optionally, step 22 is imaging subcutaneous tissue below the targeted skin surface can be between steps 10 and 12 or can be substantially simultaneous with or be part of step 12.

After step 12, step 14 is directing ultrasound energy to ROI. The ultrasound energy may be focused, defocused, or unfocused. The ultrasound sound energy can be weakly focused. The ultrasound energy can be directed to the subcutaneous tissue layer below the targeted skin surface. The ultrasound energy may be streaming. The ultrasound energy may be directed to a first depth and then directed to a second depth. The ultrasound energy may force a pressure gradient in the subcutaneous tissue layer below the targeted skin surface. The ultrasound energy may be a first ultrasound energy effect, which comprises an ablative or a hemostatic effect, and a second ultrasound energy effect, which comprises at least one of non-thermal streaming, hydrodynamic, diathermic, and resonance induced tissue effects. Directing ultrasound energy to the ROI is a non-invasive technique. As such, the targeted skin surface and the layers above a target point in the subcutaneous layer are spared from injury. Alternatively, the targeted skin surface and the layers above a target point in the subcutaneous layer are heated to a 10° C. to 15° C. above the tissue's natural state. Such treatment does not require an incision in order to reach the subcutaneous tissue layer below the targeted skin surface to enhance the targeted skin surface.

In various embodiments, the ultrasound energy level is in a range of about 0.1 joules to about 500 joules in order to create an ablative lesion. However, the ultrasound energy 108 level can be in a range of from about 0.1 joules to about 100 joules, or from about 1 joules to about 50 joules, or from about 0.1 joules to about 10 joules, or from about 50 joules to about 100 joules, or from about 100 joules to about 500 joules, or from about 50 joules to about 250 joules.

Further, the amount of time ultrasound energy is applied at these levels to create a lesion varies in the range from approximately 1 millisecond to several minutes. However, a range can be from about 1 millisecond to about 5 minutes, or from about 1 millisecond to about 1 minute, or from about 1 millisecond to about 30 seconds, or from about 1 millisecond to about 10 seconds, or from about 1 millisecond to about 1 second, or from about 1 millisecond to about 0.1 seconds, or about 0.1 seconds to about 10 seconds, or about 0.1 seconds to about 1 second, or from about 1 millisecond to about 200 milliseconds, or from about 1 millisecond to about 0.5 seconds.

The frequency of the ultrasound energy can be in a range from about 0.1 MHz to about 100 MHz, or from about 0.1 MHz to about 50 MHz, or from about 1 MHz to about 50 MHz or about 0.1 MHz to about 30 MHz, or from about 10 MHz to about 30 MHz, or from about 0.1 MHz to about 20 MHz, or from about 1 MHz to about 20 MHz, or from about 20 MHz to about 30 MHz.

The frequency of the ultrasound energy can be in a range from about 1 MHz to about 12 MHz, or from about 5 MHz to about 15 MHz, or from about 2 MHz to about 12 MHz or from about 3 MHz to about 7 MHz.

In some embodiments, the ultrasound energy can be emitted to depths at or below a skin surface in a range from about 0 mm to about 150 mm, or from about 0 mm to about 100 mm, or from about 0 mm to about 50 mm, or from about 0 mm to about 30 mm, or from about 0 mm to about 20 mm, or from about 0 mm to about 10 mm, or from about 0 mm to about 5 mm. In some embodiments, the ultrasound energy can be emitted to depths below a skin surface in a range from about 5 mm to about 150 mm, or from about 5 mm to about 100 mm, or from about 5 mm to about 50 mm, or from about 5 mm to about 30 mm, or from about 5 mm to about 20 mm, or from about 5 mm to about 10 mm. In some embodiments, the ultrasound energy can be emitted to depths below a skin surface in a range from about 10 mm to about 150 mm, or from about 10 mm to about 100 mm, or from about 10 mm to about 50 mm, or from about 10 mm to about 30 mm, or from about 10 mm to about 20 mm, or from about 0 mm to about 10 mm.

In some embodiments, the ultrasound energy can be emitted to depths at or below a skin surface in the range from about 20 mm to about 150 mm, or from about 20 mm to about 100 mm, or from about 20 mm to about 50 mm, or from about 20 mm to about 30 mm. In some embodiments, the ultrasound energy can be emitted to depths at or below a skin surface in a range from about 30 mm to about 150 mm, or from about 30 mm to about 100 mm, or from about 30 mm to about 50 mm. In some embodiments, the ultrasound energy can be emitted to depths at or below; a skin surface in a range from about 50 mm to about 150 mm, or from about 50 mm to about 100 mm. In some embodiments, the ultrasound energy can be emitted to depths at or below a skin surface in a range from about 20 mm to about 60 mm, or from about 40 mm to about 80 mm, or from about 10 mm to about 40 mm, or from about 5 mm to about 40 mm, or from about 0 mm to about 40 mm, or from about 10 mm to about 30 mm, or from about 5 mm to about 30 mm, or from about 0 mm to about 30 mm.

In various embodiments, the ultrasound energy may be emitted at various energy levels, such as for example, the energy levels described herein. Further, the amount of time ultrasound energy is applied at these levels for various time ranges, such as for example, the ranges of time described herein. The frequency of the ultrasound energy is in various frequency ranges, such as for example, the frequency ranges described herein. The ultrasound energy can be emitted to various depths below a targeted skin surface, such as for example, the depths described herein. The ultrasound energy may coagulate a portion of the subcutaneous tissue layer below the targeted skin surface. The ultrasound energy may score a portion of subcutaneous tissue layer below the targeted skin surface.

Optionally, step 24, which is administering a medicant and/or cosmeceutical to the ROI, can be between steps 12 and 14. The medicant and/or cosmeceutical can be any chemical or naturally occurring substance that can assist in cosmetic enhancement. For example the medicant and/or cosmeceutical can be but not limited to a pharmaceutical, a drug, a medication, a nutriceutical, an herb, a vitamin, a cosmetic, an amino acid, a collagen derivative, a holistic mixture, and combinations thereof.

The medicant and/or cosmeceutical can be administered by applying it to the skin above the ROI. The medicant and/or cosmeceutical can be administered to the circulatory system. For example, the medicant and/or cosmeceutical can be in the blood stream and can be activated or moved to the ROI by the ultrasound energy. The medicant and/or cosmeceutical can be administered by injection into or near the ROI. Any naturally occurring proteins, stem cells, growth factors and the like can be used as medicant and/or cosmeceutical in accordance to various embodiments. A medicant and/or cosmeceutical can be mixed in a coupling gel or can be used as a coupling gel.

Step 16 is producing a cosmetic effect in the ROI. A cosmetic effect can be an increase skin elasticity/tighten skin. A cosmetic effect can be reducing skin oiliness. A cosmetic effect can be reducing skin pore size/smooth skin texture. A cosmetic effect can be reducing hyperpigmemation. A cosmetic effect can be reducing fat and/or cellulite. A cosmetic effect can be treating and/or preventing acne. A cosmetic effect can be treating hyperhidrosis. A cosmetic effect can be reducing an appearance of spider veins and/or rosacea. A cosmetic effect can be reducing an appearance of scars. A cosmetic effect can be reducing an appearance of stretch marks. A cosmetic effect can be treatment of soft tissue. A cosmetic effect can be rejuvenation of skin. A cosmetic effect can be increasing skin elasticity. A cosmetic effect can be increasing collagen in tissue. A cosmetic effect can be a smoothing of the texture of skin. A cosmetic effect can be a tightening of sagging skin. A cosmetic effect may be the rejuvenation of photoaged skin. A cosmetic effect can be increasing a thickness of a dermal layer. A cosmetic effect can be a reduction of wrinkle on a skin surface. A cosmetic effect can be a lifting of skin, for example, a facelift, a neck lift, a brow lift, and/or a jowl lift. A cosmetic effect can be body sculpting. A cosmetic effect can be generating new tissue in the subcutaneous layer. A cosmetic effect can be synergetic with the medicant and/or cosmeceutical administered to ROI in steps 24 and/or 26. Cosmetic effects can be combined.

A cosmetic effect can be produced by a biological effect that initiated or stimulated by the ultrasound energy. A biological effect can be stimulating or increase an amount of heat shock proteins. Such a biological effect can cause white blood cells to promote healing of a portion of the subcutaneous layer in the ROI. A biological effect can be to restart or increase the wound healing cascade at the injury location. A biological effect can be increasing the blood perfusion to the injury location. A biological effect can be encouraging collagen growth. A biological effect may increase the liberation of cytokines and may produce reactive changes within the subcutaneous layer. A biological effect may by peaking inflammation in the ROI. A biological effect may be at least partially shrinking collagen in a portion of soft tissue. A biological effect may be denaturing of proteins in the ROI.

A biological effect may be creating immediate or delayed cell death (apoptosis) in the ROI. A biological effect may be collagen remodeling in the ROI. A biological effect may be the disruption or modification of biochemical cascades. A biological effect may be the production of new collagen. A biological effect may a stimulation of cell growth in the ROI. A biological effect may be angiogenesis. A biological effect may be a cell permeability response. A biological effect may be an enhanced delivery of medicants to soft tissue.

In various embodiments, ultrasound energy is deposited in the subcutaneous layer changes at least one of concentration and activity of inflammatory mediators (TNF-A, IL-1) as well as growth factors (TGF-B1, TGF-B3) below the targeted skin surface.

Optionally, step 26, which is administering medicant and/or cosmeceutical to ROI, can be between steps 14 and 16 or can be substantially simultaneous with or be part of step 16. The medicant and/or cosmeceutical useful in step 26 are essentially the same as those discussed for step 24.

In various embodiments, ultrasound energy is deposited, which can stimulate a change in at least one of concentration and activity of one or more of the following: Adrenomedullin (AM), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-a), Transforming growth factor beta (TGF-β), Tumor necrosis factor-alpha (TNF-α), Vascular endothelial growth factor (VEGF), Wnt Signaling Pathway, placental growth factor (PlGF), [(Foetal Bovine Somatotrophin)] (FBS), IL-1-Cofactor for IL-3 and IL-6, which can activate T cells, IL-2-T-cell growth factor, which can stimulate IL-1 synthesis and can activate B-cells and NK cells, IL-3, which can stimulate production of all non-lymphoid cells, IL-4-Growth factor for activating B cells, resting T cells, and mast cells, IL-5, which can induce differentiation of activated B cells and eosinophi!s, IL-6, which can stimulate Ig synthesis and growth factor for plasma cells, IL-7 growth factor for pre-B cells, and/or any other growth factor not listed herein, and combinations thereof.

Further, medicants, as described above, can include a drug, a medicine, or a protein, and combinations thereof. Medicants can also include absorbent chemicals, such as zeolites, and other hemostatic agents are used in sealing severe injuries quickly. Thrombin and fibrin glue are used surgically to treat bleeding and to thrombose aneurysms. Medicants can include Desmopressin is used to improve platelet function by activating arginine vasopressin receptor 1A. Medicants can include coagulation factor concentrates are used to treat hemophilia, to reverse the effects of anticoagulants, and to treat bleeding in patients with impaired coagulation factor synthesis or increased consumption. Prothrombin complex concentrate, cryoprecipitate and fresh frozen plasma are commonly-used coagulation factor products. Recombinant activated human factor VII can be used in the treatment of major bleeding. Medicants can include tranexamic acid and aminocaproic acid, can inhibit fibrinolysis, and lead to a de facto reduced bleeding rate. In addition, medicants can include steroids like the glucocorticoid cortisol.

Optionally, after step 12, step 25, which is directing secondary energy to the ROI can be substantially simultaneous with or be part of step 16. However, step 25 can be administered at least one of before and after step 16. Step 25 can be alternated with step 16, which can create a pulse of two different energy emissions to the ROI.

Optionally, after step 12, step 25, which is directing secondary energy to the ROI can be substantially simultaneous with or be part of step 16. However, step 25 can be administered at least one of before and after step 16. Step 25 can be alternated with step 16, which can create a pulse of two different energy emissions to the ROI. Secondary energy can be provided by a laser source, or an intense pulsed light source, or a light emitting diode, or a radio frequency, or a plasma source, or a magnetic resonance source, or a mechanical energy source, or any other photon-based energy source. Secondary energy can be provided by any appropriate energy source now known or created in the future. More than one secondary energy source may be used for step 25.

Furthermore, various embodiments provide energy, which may be a first energy and a second energy. For example, a first energy may be followed by a second energy, either immediately or after a delay period. In another example, a first energy and a second energy can be delivered simultaneously. In some embodiments, the first energy and the second energy is ultrasound energy. In some embodiments, the first energy is ultrasound and the second energy is generated by one of a laser, an intense pulsed light, a light emitting diode, a radiofrequency generator, photon-based energy source, plasma source, a magnetic resonance source, or a mechanical energy source, such as for example, pressure, either positive or negative. In other embodiments, energy may be a first energy, a second energy, and a third energy, emitted simultaneously or with a time delay or a combination thereof. In some embodiments, energy may be a first energy, a second energy, a third energy, and an nth energy, emitted simultaneously or with a time delay or a combination thereof. Any of the a first energy, a second energy, a third energy, and an nth energy may be generated by at least one of a laser, an intense pulsed light, a light emitting diode, a radiofrequency generator, an acoustic source, photon-based energy source, plasma source, a magnetic resonance source, and/or a mechanical energy source.

Step 20 is cosmetically enhancing the targeted skin surface. Optionally, between steps 16 and 20 is step 30, which is determining results. If the results of step 30 are acceptable within the parameters of the treatment then Yes direction 34 is followed to step 20. If the results of step 30 are not acceptable within the parameters of the treatment then No direction 32 is followed back to step 12. Further examples and variations of treatment method 100 are discussed herein.

Depending at least in part upon the desired bio-effect and the subcutaneous tissue being treated, method 100 may be used with an extracorporeal, non-invasive procedure. Also, depending at least in part upon the specific bio-effect and tissue targeted, temperature may increase within ROI may range from approximately 10° C. to about 15° C. Other bio-effects to target tissue can include beating, cavitation, streaming, or vibro-accoustic stimulation, and combinations thereof.

In addition, various different subcutaneous tissues may be treated by method 100 to produce different bio-effects, according to some embodiments of the present disclosure. According to various embodiments of method 100, ultrasound probe is coupled directly to ROI, as opposed to targeted skin surface 104, to affect the subcutaneous tissue.

Figure 2:
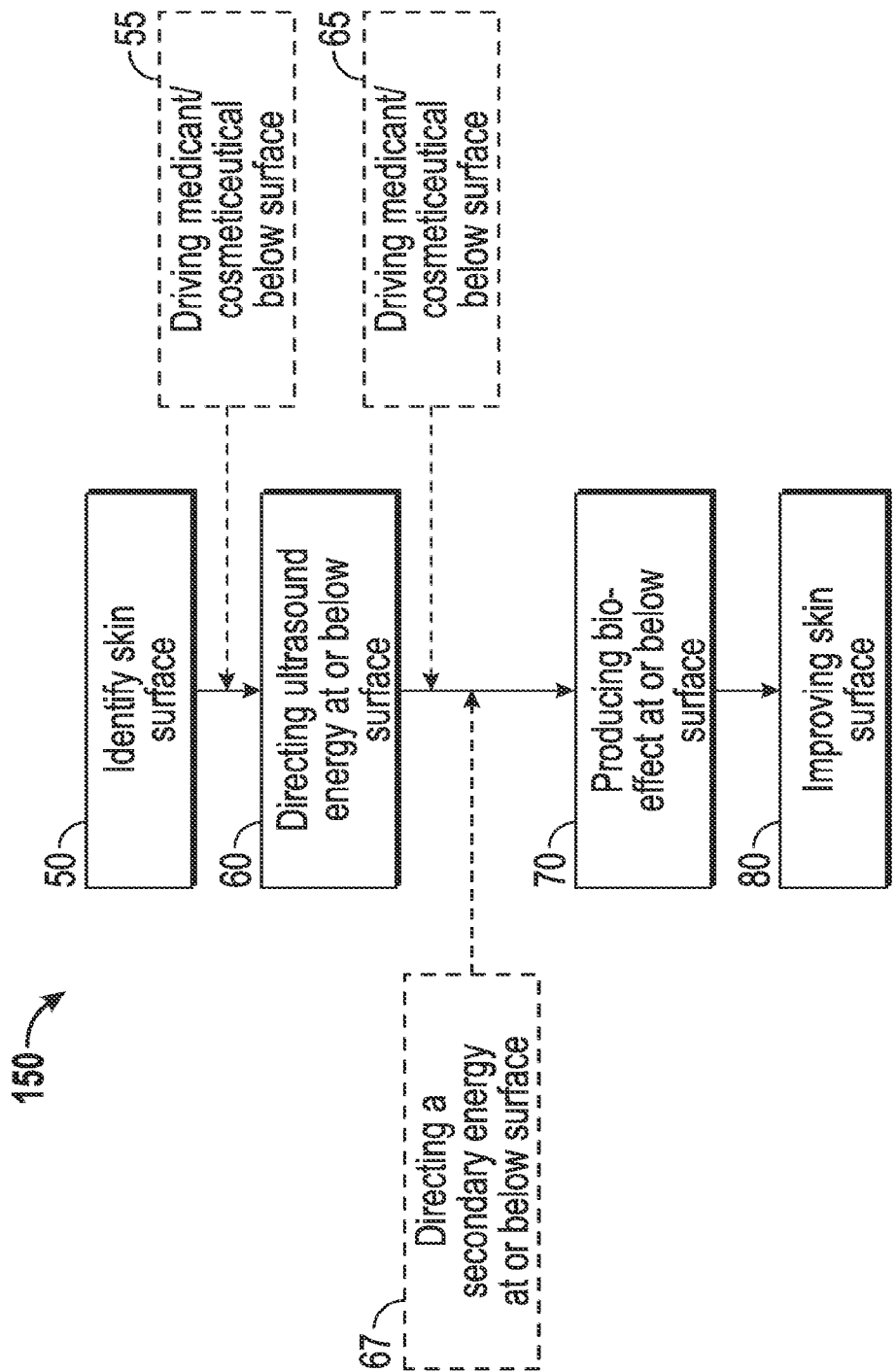
FIG. 2 is a flow chart illustrating methods according to various non-limiting embodiments.

With reference to FIG. 2, a method 150 of cosmetic rejuvenation is illustrated, which can be a subset of method 100, as illustrated in FIG. 1. Step 50 is identifying a skin surface. The skin surface can be located anywhere on the body. However, the skin surface may be located on the face and/or neck. The skin surface contains a defect or other undesirable characteristic that is to be cosmetically enhanced or rejuvenated. The defect or other undesirable characteristic may be, for example, but not limited to a wrinkle, oiliness, pore size, rough skin texture, sun spots, liver spots, sagging skin, lack of glow, a scar, a stretch mark, a blemish, and the like.

Step 60 is directing ultrasound energy into tissue below the skin surface. The ultrasound energy may be unfocused and deposited in a volume that spans from the skin surface into one or more of subcutaneous tissue below. The ultrasound energy can have any of the characteristics as described herein. The ultrasound energy can be controlled using spatial parameters. The ultrasound energy can be controlled using temporal parameters. The ultrasound energy can be controlled using a combination of temporal parameters and spatial parameters. Also, depending at least in part upon the specific bio-effect and tissue targeted, temperature of the subcutaneous tissue may increase within ROI may range from approximately 10° C. to about 15° C.

In between step 50 and step 60, option step 55 may be implemented, which is coupling a medicant or cosmeceutical to the skin surface. If step 55 is implemented, step 65 can be employed which is driving the medicant or cosmeceutical in to the subcutaneous layer below the skin surface. The medicant or cosmeceutical may be driven into the subcutaneous layer using the ultrasound energy of step 60 or an alternate frequency of ultrasound energy.

After step 60, optional step 67 can be employed, which is directing a second energy below the skin surface. The second energy can be a second ultrasound energy having different characteristics than the ultrasound energy in step 60. The second energy can be provided by a laser source, or an IPL source, or a radio frequency, or a plasma source, or a magnetic resonance source. Secondary energy can be provided by any appropriate energy source now known or created in the future. More than one secondary energy source may be used for step 67.

Step 70 is producing a bio-effect in tissue below the skin surface. A biological effect can be stimulating or increase an amount of heat shock proteins. Such a biological effect can cause white blood cells to promote healing of a portion of the subcutaneous layer in the ROI. A biological effect can be to restart or increase the wound healing cascade at the injury location. A biological effect can be increasing the blood perfusion to the injury location. A biological effect can be encouraging collagen growth. A biological effect may increase the liberation of cytokines and may produce reactive changes within the subcutaneous layer. A biological effect may by peaking inflammation in the ROI. A biological effect may at least partially shrinking collagen portion of soft tissue. A biological effect may be denaturing of proteins in the ROI.

A biological effect may be creating immediate or delayed cell death (apoptosis) in the ROI. A biological effect may be collagen remodeling in the ROI. A biological effect may be the disruption or modification of biochemical cascades. A biological effect may be the production of new collagen. A biological effect may be a stimulation of cell growth in the ROI. A biological effect may be angiogenesis. A biological effect may be a cell permeability response. A biological effect may be an enhanced delivery of medicants to soft tissue.

Step 80 is improving an appearance of the skin surface. This can be a cosmetic effect. The improving an appearance of the skin surface can be an increase in skin elasticity. The improving an appearance of the skin surface can be reducing skin oiliness. The improving an appearance of the skin surface can be reducing skin pore size. The improving an appearance of the skin surface can be smoothing skin texture. The improving an appearance of the skin surface can be reducing hyperpigmentation. The improving an appearance of the skin surface can be treating and/or preventing acne. The improving an appearance of the skin surface can be reducing a blemish. The improving an appearance of the skin surface can be reducing an appearance of spider veins and/or rosacea. The improving an appearance of the skin surface can be reducing an appearance of scars. The improving an appearance of the skin surface can be reducing an appearance of stretch marks. The improving an appearance of the skin surface can be rejuvenation of skin. The improving an appearance of the skin surface can be increasing collagen in tissue. The improving an appearance of the skin surface can be a tightening of sagging sink. The improving an appearance of the skin surface can be the rejuvenation of photoaged skin. The improving an appearance of the skin surface can be increasing a thickness of a dermal layer. The improving an appearance of the skin surface can be a reduction of wrinkle on a skin surface. The improving an appearance of the skin surface can be generating new tissue in the subcutaneous layer. The improving an appearance of the skin surface can be synergetic with the medicant and/or cosmeceutical administered to ROI in steps 55 and 65.

Figure 3:
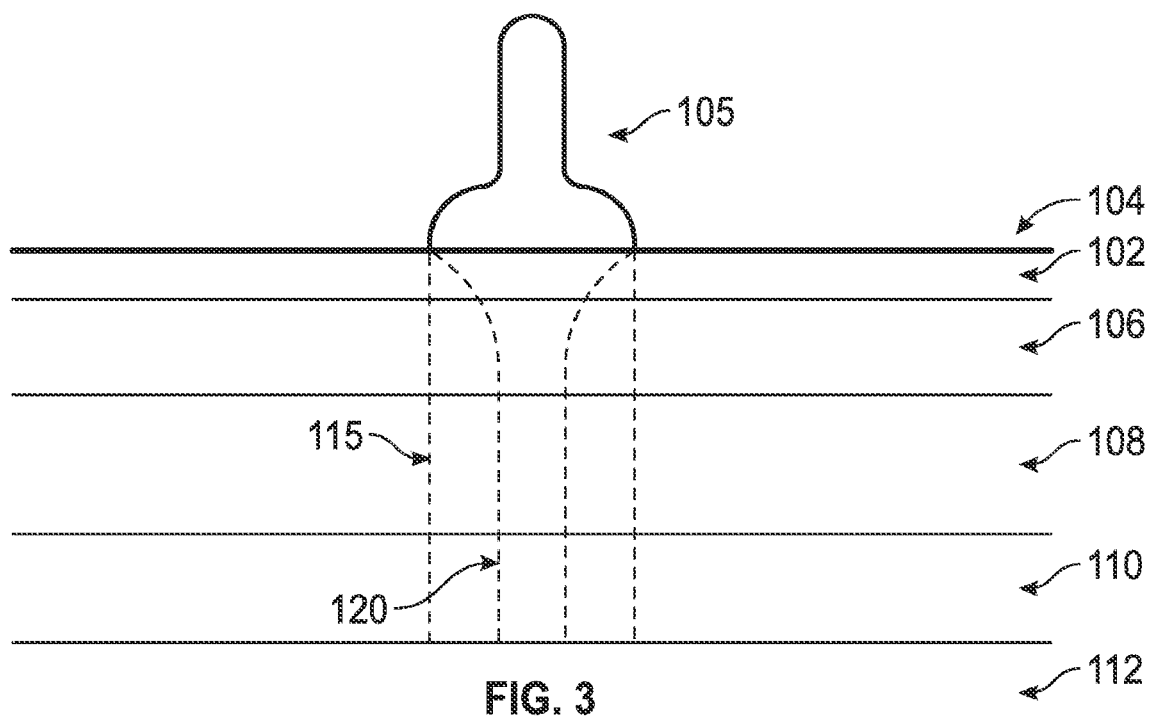
FIG. 3 is a cross sectional view illustrating ultrasound energy directed to various subcutaneous tissue layers below a surface, according to various non-limiting embodiments.

Now moving to FIG. 3, a cross sectional view of tissue layers and ultrasound energy directed to a subcutaneous layer, according to various embodiments, is illustrated. Typically, ultrasound energy propagates as a wave with relatively little scattering, over depths up to many centimeters in tissue depending on the ultrasound frequency. The focal spot size achievable with any propagating wave energy depends on wavelength. Ultrasound wavelength is equal to the acoustic velocity divided by the ultrasound frequency. Attenuation (absorption, mainly) of ultrasound by tissue also depends on frequency. Shaped conformal distribution of elevated temperature can be created through adjustment of the strength, depth, and type of focusing, energy levels and timing cadence. For example, focused ultrasound can be used to create precise arrays of microscopic thermal ablation zones. Ultrasound energy 120 can produce an array of ablation zones deep into the layers of the soft tissue. Detection of changes in the reflection of ultrasound energy can be used for feedback control to detect a desired effect on the tissue and used to control the exposure intensity, time, and/or position.

In various embodiment, ultrasound probe 105 is configured with the ability to controllably produce conformal distribution of elevated temperature in soft tissue within ROI 115 through precise spatial and temporal control of acoustic energy deposition, i.e., control of ultrasound probe 105 is confined within selected time and space parameters, with such control being independent of the tissue. The ultrasound energy 120 can be controlled using spatial parameters. The ultrasound energy 120 can be controlled using temporal parameters. The ultrasound energy 120 can be controlled using a combination of temporal parameters and spatial parameters.

In accordance with various embodiments, control system and ultrasound probe 105 can be configured for spatial control of ultrasound energy 120 by controlling the manner of distribution of the ultrasound energy 120. For example, spatial control may be realized through selection of the type of one or more transducer configurations insonifying ROI 115, selection of the placement and location of ultrasound probe 105 for delivery of ultrasound energy 120 relative to ROI 115 e.g., ultrasound probe 105 being configured for scanning over part or whole of ROI 115 to produce contiguous thermal injury having a particular orientation or otherwise change in distance from ROI 115, and/or control of other environment parameters, e.g., the temperature at the acoustic coupling interface can be controlled, and/or the coupling of ultrasound probe 105 to tissue. Other spatial control can include but are not limited to geometry configuration of ultrasound probe 105 or transducer assembly, lens, variable focusing devices, variable focusing lens, stand-offs, movement of ultrasound probe, in any of six degrees of motion, transducer backing, matching layers, number of transduction elements in transducer, number of electrodes, or combinations thereof.

In various embodiments, control system and ultrasound probe 105 can also be configured for temporal control, such as through adjustment and optimization of drive amplitude levels, frequency, waveform selections, e.g., the types of pulses, bursts or continuous waveforms, and timing sequences and other energy drive characteristics to control thermal ablation of tissue. Other temporal control can include but are not limited to full power burst of energy, shape of burst, timing of energy bursts, such as, pulse rate duration, continuous, delays, etc., change of frequency of burst, burst amplitude, phase, apodization, energy level, or combinations thereof.

The spatial and/or temporal control can also be facilitated through open-loop and closed-loop feedback arrangements, such as through the monitoring of various spatial and temporal characteristics. As a result, control of acoustical energy within six degrees of freedom, e.g., spatially within the X, Y and Z domain, as well as the axis of rotation within the XY, YZ and XZ domains, can be suitably achieved to generate conformal distribution of elevated temperature of variable shape, size and orientation. For example, through such spatial and/or temporal control, ultrasound probe 105 can enable the regions of elevated temperature possess arbitrary shape and size and allow the tissue to be heated in a controlled manner.

The subcutaneous tissue 127 layers illustrated are targeted skin surface 104, epidermal layer 102, dermis layer 106, fat layer 108, SMAS layer 110, and muscle and connective tissue layer 112. Ultrasound probe 105 emits ultrasound energy 120 in ROI 115. In various embodiments, ultrasound probe 105 is capable of emitting ultrasound energy 120 at variable: depths in ROI 115, such as, for example, the depths described herein. Ultrasound probe 105 is capable of emitting ultrasound energy as a single frequency, variable frequencies, or a plurality of frequencies, such as, for example, the frequency ranges described herein. Ultrasound probe 105 is capable of emitting ultrasound energy that is weakly focused. Ultrasound probe 105 is capable of emitting ultrasound energy 120 for variable time periods or to pulse the emission over time, such as, for example, those time intervals described herein. Ultrasound probe 105 is capable of providing various energy levels of ultrasound energy, such as, for example, the energy levels described herein.

Ultrasound probe 105 may be individual hand-held device, or may be part of a treatment system. The ultrasound probe 105 can provide both ultrasound energy and imaging ultrasound energy. However, ultrasound probe 105 may provide only ultrasound energy. Ultrasound probe 105 may comprise a therapeutic transducer and a separate imaging transducer. Ultrasound probe 105 may comprise a transducer or a transducer array capable of both cosmetic rejuvenation and imaging applications. Accordingly an alternative embodiment, ultrasound probe 105 is coupled directly to one of the tissue layers, as opposed to targeted skin surface 104 to treat the tissue layer.

In various embodiments, ultrasound probe 105 may be used for method 100 or method 150, In various embodiments, method 100 or method 150 can be implemented using any or all of the elements illustrated in FIG. 3. As will be appreciated by those skilled in the art, at least a portion of method 100 or a variation of method 100 can be implemented using any or all of the elements illustrated in FIG. 3. Furthermore, at least a portion of method 150 or a variation of method 150 can be implemented using any or all of the elements illustrated in FIG. 3.

Figure 4:
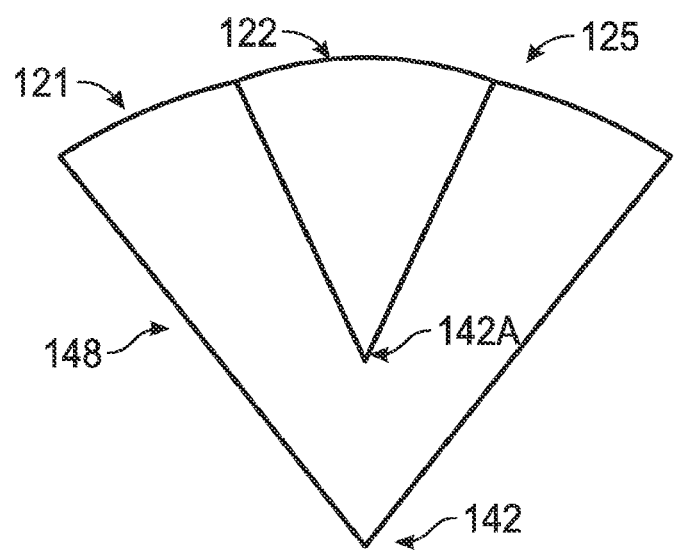
FIG. 4 is a cross sectional view illustrating ultrasound energy directed to two targets in subcutaneous tissue below a surface, according to various non-limiting embodiments.

With reference to FIG. 4, an embodiment of transduction element 125 is illustrated. Transduction element 125B comprises first transduction element 121 and second transduction element 122. In some embodiments, first transduction element 121 and second transduction element 122 can have the same focus, which can be mechanical focus, electronic focus, or combinations thereof. In some embodiments, first transduction element 121 and second transduction element 122 can have different focal points. In some embodiments, first transduction element 121 and second transduction element 122 can be multiple elements of the same therapy transducer, sectioned for different f-numbers.

In some embodiments, first transduction element 121 is operable to focus ultrasound energy 148 to target zone 142 and second transduction element 122 is operable to focus ultrasound energy 108 to second target zone 142A. Alternatively, first transduction element 121 and second transduction element 122 may be controlled in a combination of different frequencies, different time periods, and different power levels to focus ultrasound energy 148 to at least one of target zone 142 and second target zone 142A.

Figure 5:
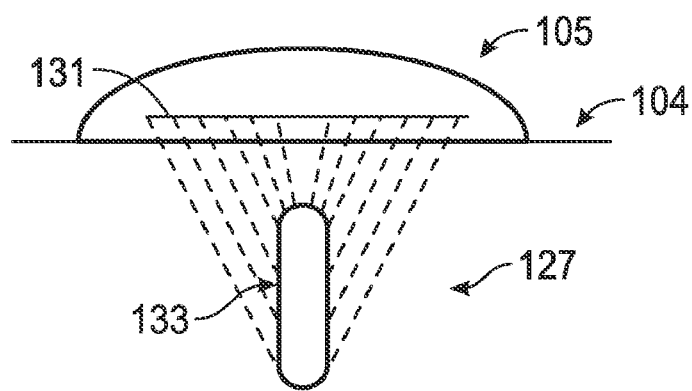
FIG. 5 is a cross sectional view illustrating a conformal region of elevated temperature in subcutaneous tissue, according to various non-limiting embodiments.
Figure 6:
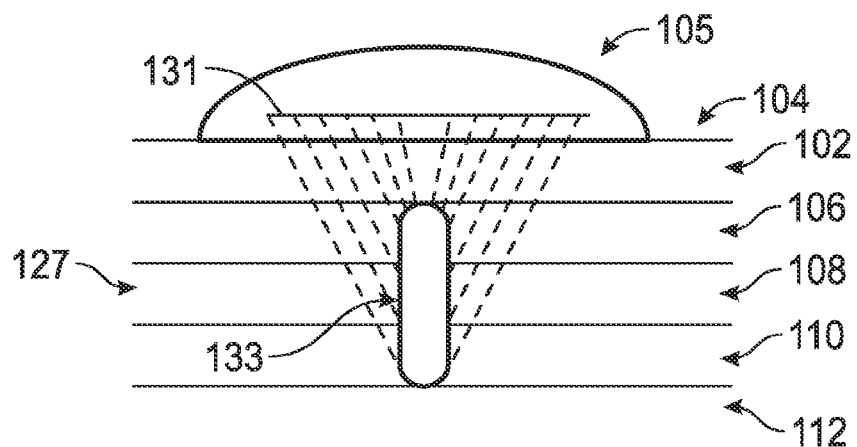
FIG. 6 is a cross sectional view illustrating a conformal region of elevated temperature in various layers of subcutaneous tissue, according to various non-limiting embodiments.

Now with reference to FIGS. 5 and 6, an embodiment of a probe 105 comprising an annular array 131 of transduction elements is illustrated. Annular array 131 can be controlled to weakly focused ultrasound energy 133 into subcutaneous layer 127. The weakly focused ultrasound energy 133 is controlled to create a conformal region 133 of elevated temperature in the subcutaneous layer 127. The conformal region 133 of elevated temperature can be directed to one or more layers of skin or one or more layers of subcutaneous tissue 127.

For example, the conformal region 133 of elevated temperature may be directed to span from skin surface 104 to the epidermal layer 102. For example, the conformal region 133 of elevated temperature may be directed to span from skin surface 104, through the epidermal layer 102, to at least a portion of the dermal layer 106. For example, the conformal region 133 of elevated temperature may include targeted skin surface 104, epidermal layer 102, dermis layer 106, and fat layer 108. For example, the conformal region 133 of elevated temperature may include targeted skin surface 104, epidermal layer 102, dermis layer 106, fat layer 108, and SMAS layer 110. For example, the conformal region 133 of elevated temperature may include targeted skin surface 104, epidermal layer 102, dermis layer 106, fat layer 108, and SMAS layer 110. For example, the conformal region 133 of elevated temperature may include targeted skin surface 104, epidermal layer 102, dermis layer 106, fat layer 108, SMAS layer 110 and muscle layer 112.

Alternately, the conformal region 133 of elevated temperature may include epidermal layer 102, dermis layer 106, fat layer 108, SMAS layer 110 and muscle layer 112. The conformal region 133 of elevated temperature may include dermis layer 106, fat layer 108, SMAS layer 110 and muscle layer 112. The conformal region 133 of elevated temperature may include SMAS layer 110 and muscle layer 112. The conformal region 133 of elevated temperature may include the muscle layer 112.

In another example, the conformal region 133 of elevated temperature may include epidermal layer 102, dermis layer 106, fat layer 108, and SMAS layer 110. The conformal region 133 of elevated temperature may include dermis layer 106, fat layer 108, and SMAS layer 110. The conformal region 133 of elevated temperature may include fat layer 108, and SMAS layer 110. The conformal region 133 of elevated temperature may include SMAS layer 110.

In still another example, the conformal region 133 of elevated temperature may include targeted skin surface 104, epidermal layer 102, dermis layer 106, and fat layer 108. The conformal region 133 of elevated temperature may include targeted skin surface 104, epidermal layer 102, dermis layer 106, and fat layer 108. The conformal region 133 of elevated temperature may include dermis layer 106, and fat layer 108, The conformal region 133 of elevated temperature may include dermis the fat layer 108. For example, the conformal region 133 of elevated temperature may include targeted skin surface 104, epidermal layer 102, and dermis layer 106. The conformal region 133 of elevated temperature may include epidermal layer 102, and dermis layer 106. The conformal region 133 of elevated temperature may include the dermis layer 106. In another example, the conformal region 133 of elevated temperature may include targeted skin surface 104 and the epidermal layer 102. The conformal region 133 of elevated temperature may include the epidermal layer 102. The conformal region 133 of elevated temperature may include targeted skin surface 104. In still another example, the conformal region 133 of elevated temperature may include a junction between the dermis layer 106 and the SMAS layer 110.

Figure 7:
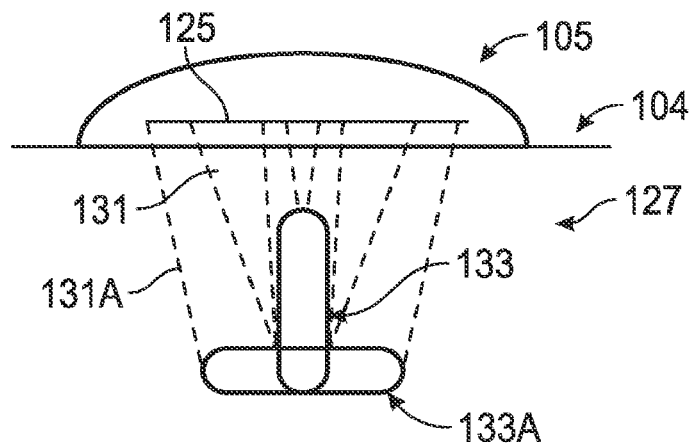
FIG. 7 is a cross sectional view illustrating conformal region of elevated temperature and second conformal region of elevated temperature in subcutaneous tissue, according to various non-limiting embodiments.
Figure 8:
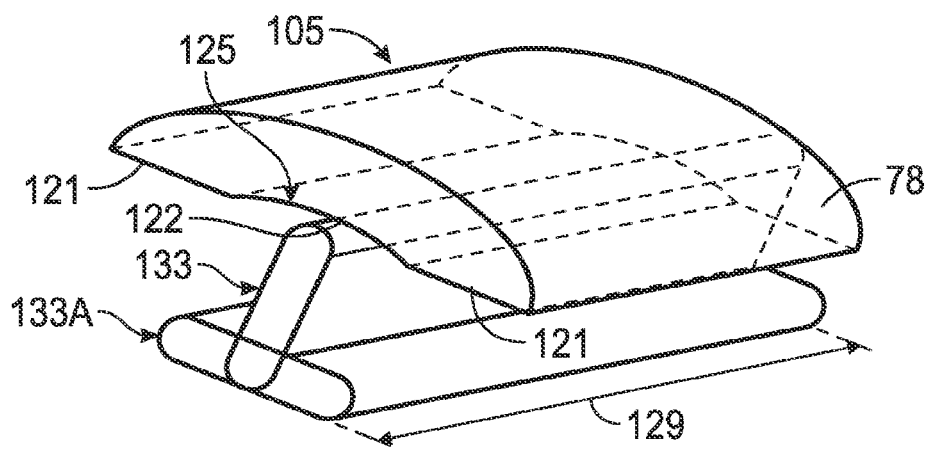
FIG. 8 is a prospective view illustrating conformal region of elevated temperature and second conformal region of elevated temperature in subcutaneous tissue, according to various non-limiting embodiments.
Figure 9:
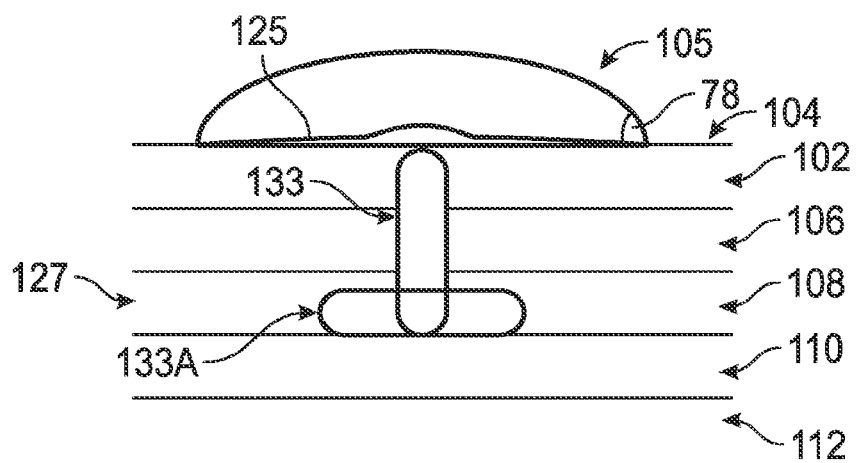
FIG. 9 is a cross sectional view illustrating conformal region of elevated temperature and second conformal region of elevated temperature in various layers of subcutaneous tissue, according to various non-limiting embodiments.

In FIGS. 7-11, transducer 125 is configured to create conformal region 133 of elevated temperature and second conformal region 133A, in accordance to various embodiments. In various embodiments, ultrasound probe 105 comprises enclosure 78 containing transducer 125 and optionally position sensor 107. Ultrasound probe 105 can be coupled to targeted skin surface 104. Ultrasound energy 131 and 131A can be emitted by transducer 125 to create conformal region 133 of elevated temperature and second conformal region 133A of elevated temperature in subcutaneous tissue 127. In various embodiments, weakly focused ultrasound energy 131 and second weakly focused ultrasound energy 131A can create conformal region 133 of elevated temperature and second conformal region 133A. In some embodiments, conformal region 133 of elevated temperature and second conformal region 133A intersect. As illustrated in FIG. 7, transducer 125 is elongated and may comprise a plurality of transduction elements. In this configuration, transducer 125 can create conformal region 133 of elevated temperature and second conformal region 133A along dimension 129. In this configuration, probe 105 can provide a cosmetic effect to a larger area of targeted skin surface 104.

As discussed herein, conformal region 133 of elevated temperature can be directed to one or more layers of skin or one or more layers of subcutaneous tissue 127. Accordingly, second conformal region 133A of elevated temperature can be directed to one or more layers of skin or one or more layers of subcutaneous tissue 127, as described herein in regards to conformal region 133 of elevated temperature. In some embodiments, at least a portion both conformal region 133 of elevated temperature and second conformal region 133A of elevated temperature are directed to the same layer of combination of layers in the subcutaneous tissue 127.

Now with reference to FIG. 12, ultrasound probe 105 is illustrated. In various embodiments, ultrasound probe 105 comprises enclosure 78 containing transducer 125 and optionally position sensor 107. Ultrasound probe 105 can be coupled to targeted skin surface 104. Ultrasound energy 131 and 131A can be emitted by transducer 125 to create conformal region 133 of elevated temperature and second conformal region 133A of elevated temperature in subcutaneous tissue 127. In various embodiments, weakly focused ultrasound energy 131 and second weakly focused ultrasound energy 131A can create conformal region 133 of elevated temperature and second conformal region 133A.

In various embodiments, position sensor 107 may determine a distance 117 between pulses of therapeutic ultrasound energy 108 to create a plurality of conformal region 133 of elevated temperature which are evenly spaced or disposed in any spatial configuration in one-, two-, or three-dimensions. As ultrasound probe 105 is moved in direction 130, position sensor 107 determines distance 117, regardless of a speed that ultrasound probe 105 is move, at which a pulse of ultrasound energy 131 or 131A is to be emitted in to ROI. In various embodiments ultrasound probe 105 is triggered automatically via a timer and in combination with a position sensor 107 to assure motion.

However, in various embodiments, ultrasound probe 105 comprises position sensor 107. Position sensor 107 can be integrated into ultrasound probe 105 or attached to ultrasound probe 105. In an exemplary embodiment, position sensor 107 is a motion sensor measuring position of ultrasound probe 105. Such a motion sensor can calculate distance traveled along skin surface 104. Such a motion sensor may determine a speed of movement of ultrasound probe 105 along skin surface 104 and determine if the speed is accurate for the cosmetic procedure that is elected. For example if the speed is too fast, motion sensor can signal an indicator to slow the speed and/or can signal transducer 125 to stop emitting ultrasound energy 131 and 131A.

In various embodiments, position sensor 107 can include a laser position sensor. For example, position sensor 107 can track position like a computer mouse that uses a laser sensor as opposed to an older version of a mouse with a roller ball. Position sensor 107 can communicate position data versus time to a display to track a position of ultrasound probe 105, such as, for example, overlaid on an image of ROI, overlaid on an image of skin surface 104, as referenced to geotagged features, as reference to targeted location, as referenced to prior procedures, and combinations thereof. In an exemplary a treatment plan can include a movement pattern of ultrasound probe 105. Such a movement pattern can be displayed and the position sensor 107 can track a position of ultrasound probe 105 during a cosmetic procedure as compared to the movement pattern. Tracking ultrasound probe 105 with position sensor and comparing the tracked movement to a predetermined movement may be useful as a training tool. In an exemplary embodiment laser position sensor can geotag a feature on skin surface 104.

In various embodiments, position sensor 107 may determine a distance 117 between pulses of therapeutic ultrasound energy 108 to create a plurality of lesions 25 which are evenly spaced or disposed in any spatial configuration in one-, two-, or three-dimensions. As ultrasound probe 105 is moved in direction 130, position sensor 107 determines distance 117, regardless of a speed that ultrasound probe 105 moves, at which a pulse of therapeutic ultrasound energy 108 is to be emitted in to ROI. In various embodiments ultrasound probe 105 is triggered automatically via a timer and in combination with a position sensor 107 to assure motion.

Position sensor 107 may be located behind a transducer, in front of a transducer array, or integrated into a transducer array. Ultrasound probe 105 may comprise more than one position sensor 107, such as, for example a laser position sensor and a motion sensor, or a laser position sensor and a visual device, or a motion sensor and a visual device, or a laser position sensor, a motion sensor, and a visual device. Additional embodiments of position sensor 107 may be found in U.S. Pat. No. 7,142,905, entitled "Visual Imaging System for Ultrasonic Probe" issued Nov. 28, 2006, and U.S. Pat. No. 6,540,679, entitled "Visual Imaging System for Ultrasonic Probe" issued Apr. 1, 2003, both of which are incorporated by reference.

Position sensor 107 can be integrated into ultrasound probe 105 or attached to ultrasound probe 105. In an exemplary embodiment, position sensor 107 is an optical sensor measuring 1-D, 2-D, or 3-D movement 130 of ultrasound probe 105 versus time while probe travels along skin surface 104. Such a position sensor may control conformal region 133 of elevated temperature sequence directly, by using position information in the treatment system to trigger emission of ultrasound energy 131 and 131A. In various embodiments, cosmetic enhancement can be triggered when the ultrasound probe 105 reaches a fixed or predetermined range away from the last ablation zone 112. Speed of motion can be used to control therapeutic ultrasound energy 108. For example, if the motion is too fast information can be provided to the user to slow down and/or energy can be dynamically adjusted within limits. Position information may also be used to suppress energy if crossing over the same spatial position, if desired. Such a position sensor 107 may also determine if ultrasound probe 105 is coupled to skin surface 104, to safely control energy delivery and provide information to users.

With reference to FIG. 13, a hand held ultrasound probe, according to various embodiments of the present invention, is illustrated. In various embodiments, ultrasound probe 105 comprises transducer 125, as described herein, and may be controlled and operated by a hand-held format control system. An external battery charger can be used with rechargeable-type batteries 84 or the batteries 84 can be single-use disposable types, such as M-sized cells. Power converters produce voltages for powering a driver/feedback circuit with tuning network driving transducer array 100.

Ultrasound probe 105 is coupled to targeted skin surface 104 via one or more tips 88, which can be composed of at least one of a solid media, semi-solid, such as, for example, a gelatinous media, and liquid media equivalent to an acoustic coupling agent contained within a housing in tip. Tip 88 is coupled to targeted skin surface 104 with an acoustic coupling agent. In some embodiments, ultrasound probe 105 comprises position sensor 107, as described herein. In some embodiments, tip 88 may comprise transducer 125. In such embodiments, the tip 88 and transducer 125 can be disposable and replaceable.

In addition, a microcontroller and timing circuits with associated software and algorithms provide control and user interfacing via a display or LED-type indicators 83, and other input/output controls 82, such as switches and audio devices. A storage element, such as an Electrically Erasable Programmable Read-Only Memory ("EEPROM"), secure EEPROM, tamper-proof EEPROM, or similar device can hold calibration and usage data. A motion mechanism with feedback can be controlled to scan the transducer 125 in a linear pattern or a two-dimensional pattern or over a varied depth. Other feedback controls comprise capacitive, acoustic, or other coupling detection means, limiting controls, and thermal sensor, EEPROM can be coupled with at least one of tip 88, transducer array 100, thermal sensor, coupling detector, and tuning network. Data from EEPROM can be collected in controller 144 and connected to treatment data.

In an exemplary embodiment, data from EEPROM can be downloaded to a user's computer via any interface type, such as, for example, a USB interface, a RS 232 interface, a IEEE interface, a fire-wire interface, a blue tooth interface, an infrared interface, a 802.1 interface, via the web, and the like. Downloadable data can include hours of use, frequency during use, power levels, depths, codes from tips used, error codes, user ID, and other such data. The data can be parsed by user ID so more than one user can track user data. Similarly, EEPROM can be interfaced, using any of the methods or devices described herein, to a computer or the web to receive software updates. Still further, EEPROM can be interfaced, using any of the methods or devices described herein, to a computer or the web for at least one of diagnosis, trouble shooting, service, repair, and combinations thereof.

As illustrated in FIG. 13, ultrasound probe 105 can be m communication with wireless device 200 via wireless interface 204. Typically, wireless device 200 has display 206 and a user interface such as, for example, a keyboard. Examples of wireless device 200 can include but are not limited to: personal data assistants ("PDA"), cell phone, iPhone, iPad, computer, laptop, netbook, or any other such device now known or developed in the future. Examples of wireless interface 204 include but are not limited to any wireless interface described herein and any such wireless interface now known or developed in the future. Accordingly, ultrasound probe 105 comprises any hardware, such as, for example, electronics, antenna, and the like, as well as, any software that may be used to communicate via wireless interface 204.

In various embodiments, device 200 can display an image generated by handheld probe 105. In various embodiments, device 200 can control handheld ultrasound probe 105. In various embodiments, device 200 can store data generated by handheld ultrasound probe 105.

In various embodiments, transducer 125, optionally and imaging transducer array 110, and optionally, position sensor 107 can held within enclosure 78. In an exemplary embodiment, enclosure 78 is designed for comfort and control while used in an operator's hand. Enclosure 78 may also contain various electronics, such as, for example, EEPROM, interface connection, motion mechanisms, and/or ram for holding programs, and combinations thereof.

Ultrasound energy 131 and 131A from transducer 125 may be spatially and/or temporally controlled at least in part by changing the spatial parameters of transducer 125, such as the placement, distance, treatment depth and transducer 125 structure, as well as by changing the temporal parameters of transducer 125, such as the frequency, drive amplitude, and timing, with such control handled via controller in hand-held assembly of ultrasound probe 105. In various embodiments, ultrasound probe 105 comprises a transducer 125 capable of emitting ultrasound energy 131 and 131A into ROI. This may heat ROI at a specific depth to target tissue as described herein.

Ultrasound energy 131 creates conformal region 133 of elevated temperature in a tissue layer, at which a temperature of tissue is raised by 10° C. to 15° C., or is raised to a temperature in the range from about 4° C. to about 55° C., or from about 43° C. to about 48° C., or below a threshold of ablation of the tissue.

In various embodiments, the ultrasound energy level is in a range of about 0.1 joules to about 500 joules in order to create an ablative lesion. However, the ultrasound energy 108 level can be in a range of from about 0.1 joules to about 100 joules, or from about 1 joules to about 50 joules, or from about 0.1 joules to about 10 joules, or from about 50 joules to about 100 joules, or from about 100 joules to about 500 joules, or from about 50 joules to about 250 joules.

Further, the amount of time ultrasound energy is applied at these levels to create a lesion varies in the range from approximately 1 millisecond to several minutes. However, a range can be from about 1 millisecond to about 5 minutes, or from about 1 millisecond to about 1 minute, or from about 1 millisecond to about 30 seconds, or from about 1 millisecond to about 10 seconds, or from about 1 millisecond to about 1 second, or from about 1 millisecond to about 0.1 seconds, or about 0.1 seconds to about 10 seconds, or about 0.1 seconds to about 1 second, or from about 1 millisecond to about 200 milliseconds, or from about 1 millisecond to about 0.5 seconds.

The frequency of the ultrasound energy can be in a range from about 0.1 MHz to about 100 MHz, or from about 0.1 MHz to about 50 MHz, or from about 1 MHz to about 50 MHz or about 0.1 MHz to about 30 MHz, or from about 10 MHz to about 30 MHz, or from about 0.1 MHz to about 20 MHz, or from about 1 MHz to about 20 MHz, or from about 20 MHz to about 30 MHz.

The frequency of the ultrasound energy can be in a range from about 1 MHz to about 12 MHz, or from about 5 MHz to about 15 MHz, or from about 2 MHz to about 12 MHz or from about 3 MHz to about 7 MHz.

In some embodiments, the ultrasound energy can be emitted to depths at or below a skin surface in a range from about 0 mm to about 150 mm, or from about 0 mm to about 100 mm, or from about 0 mm to about 50 mm, or from about 0 mm to about 30 mm, or from about 0 mm to about 20 mm, or from about 0 mm to about 10 mm, or from about 0 mm to about 5 mm. In some embodiments, the ultrasound energy can be emitted to depths below a skin surface in a range from about 5 mm to about 150 mm, or from about 5 mm to about 100 mmn, or from about 5 mm to about 50 mm, or from about 5 mm to about 30 mm, or from about 5 mm to about 20 mm, or from about 5 mm to about 10 mm. In some embodiments, the ultrasound energy can be emitted to depths below a skin surface in a range from about 10 mm to about 150 mm, or from about 10 mm to about 100 mm, or from about 10 mm to about 50 mm, or from about 10 mm to about 30 mm, or from about 10 mm to about 20 mm, or from about 0 mm to about 10 mm.

In some embodiments, the ultrasound energy can be emitted to depths at or below a skin surface in the range from about 20 mm to about 150 mm, or from about 20 mm to about 100 mm, or from about 20 mm to about 50 mm, or from about 20 mm to about 30 mm. In some embodiments, the ultrasound energy can be emitted to depths at or below a skin surface in a range from about 30 mm to about 150 mm, or from about 30 mm to about 100 mm, or from about 30 mm to about 50 mm. In some embodiments, the ultrasound energy can be emitted to depths at or below a skin surface in a range from about 50 mm to about 150 mm, or from about 50 mm to about 100 mm. In some embodiments, the ultrasound energy can be emitted to depths at or below a skin surface in a range from about 20 mm to about 60 mm, or from about 40 mm to about 80 mm, or from about 10 mm to about 40 mm, or from about 5 mm to about 40 mm, or from about 0 mm to about 40 mm, or from about 10 mm to about 30 mm, or from about 5 mm to about 30 mm, or from about 0 mm to about 30 mm.

In various embodiments, the probe 105 comprises a transducer 125 operating frequency range of 2-12 MHz or 4-8 MHz or 6 MHz. In various embodiments, the probe 105 comprises a transducer 125 with an operating power of about 1 watt. In various embodiments, the probe 105 comprises a transducer 125 having an operating intensity range: 10-500 W/cm$^2$ or 20-100 W/cm$^2$. In various embodiments, the probe 105 comprises a transducer 125 that is a consumable transducer.

Further, medicant and/or cosmeceutical, as described above, can include a drug, a medicine, or a protein, and combinations thereof. Medicant and/or cosmeceutical can also include a vaccine, blood or blood component, allergenic, somatic cell, gene therapy, tissue, recombinant therapeutic protein, or living cells that are used as therapeutics to treat diseases or as actives to produce a cosmetic effect. Medicant and/or cosmeceutical can also include a biologic, such as for example a recombinant DNA therapy, synthetic growth hormone, monoclonal antibodies, or receptor constructs.

Medicant and/or cosmeceutical can also include adsorbent chemicals, such as zeolites, and other hemostatic agents are used in sealing severe injuries quickly. Thrombin and fibrin glue are used surgically to treat bleeding and to thrombose aneurysms. Medicant and/or cosmeceutical can include Desmopressin is used to improve platelet function by activating arginine vasopressin receptor 1A. Medicant and/or cosmeceutical can include coagulation factor concentrates are used to treat hemophilia, to reverse the effects of anticoagulants, and to treat bleeding in patients with impaired coagulation factor synthesis or increased consumption. Prothrombin complex concentrate, cryoprecipitate and fresh frozen plasma are commonly-used coagulation factor products. Recombinant activated human factor VII can be used in the treatment of major bleeding. Medicant and/or cosmeceutical can include tranexamic acid and aminocaproic acid, can inhibit fibrinolysis, and lead to a de facto reduced bleeding rate. In addition, medicant and/or cosmeceutical can include steroids like the glucocorticoid cortisol. A medicant and/or cosmeceutical can include compounds as alpha lipoic Acid, DMAE, vitamin C ester, tocotrienols, and phospholipids.

Medicant 202 can be a pharmaceutical compound such as for example, cortisone, Etanercept, Abatacept, Adalimumab, or Infliximab. Medicant 202 can include platelet-rich plasma (PRP), mesenchymal stem cells, or growth factors. For example, PRP is typically a fraction of blood that has been centrifuged. The PRP is then used for stimulating healing of the injury. The PRP typically contains thrombocytes (platelets) and cytokines (growth factors). The PRP may also contain thrombin and may contain fibrinogen, which when combined can form fibrin glue. Medicant 202 can be a prothrombin complex concentrate, cryoprecipitate and fresh frozen plasma, which are commonly-used coagulation factor products. Medicant 202 can be a recombinant activated human factor VII, which can be used in the treatment of major bleeding. Medicant 202 can include tranexamic acid and aminocaproic acid, can inhibit fibrinolysis, and lead to a de facto reduced bleeding rate. In some embodiments, medicant can be Botox.

A medicant and/or cosmeceutical can include platelet-rich plasma (PRP), mesenchymal stem cells, or growth factors. For example, PRP is typically a fraction of blood that has been centrifuged. The PRP is then used tor stimulating healing of the injury. The PRP typically contains thrombocytes (platelets) and cytokines (growth factors). The PRP may also contain thrombin and may contain fibrinogen, which when combined can form fibrin glue.

The following patents and patent applications are incorporated by reference: —US Patent Application Publication No. 20050256406, entitled "Method and System for Controlled Scanning, Imaging, and/or Therapy" published Nov. 17, 2005; US Patent Application Publication No. 20060058664, entitled "System and Method for Variable Depth Ultrasound Treatment" published Mar. 16, 2006; US Patent Application Publication No, 20060084891, entitled Method and System for Ultra-High Frequency Ultrasound Treatment" published Apr. 20, 2006; U.S. Pat. No. 7,530,958, entitled "Method and System for Combined Ultrasound Treatment" issued May 12, 2009; US Patent Application Publication No. 2008071255, entitled "Method and System for Treating Muscle, Tendon, Ligament, and Cartilage Tissue" published Mar. 20, 2008; U.S. Pat. No. 6,623,430, entitled "Method and Apparatus for Safely Delivering Medicants to a Region of Tissue Using Imaging, Therapy, and Temperature Monitoring Ultrasonice System, issued Sep. 23, 2003; U.S. Pat. No. 7,571,336, entitled "Method and System for Enhancing Safety with Medical Peripheral Device by Monitoring if Host Computer is AC Powered" issued Aug. 4, 2009; US Patent Application Publication No. 20080281255, entitled "Methods and Systems for Modulating Medicants Using Acoustic Energy" published Nov. 13, 2008; US Patent Application Publication No. 20060116671, entitled "Method and System for Controlled Thermal Injury of Human Superficial Tissue," published Jun. 1, 2006; US Patent Application Publication No. 20060111744, entitled "Method and System for Treatment of Sweat Glands," published May 25, 2006; US Patent Application Publication No. 20080274073, entitled "Method and System for Non-Ablative Acne Treatment and Prevention," published Oct. 8, 2009; U.S. Pat. No. 8,133,180, entitled "Method and System for Treating Cellulite," issued Mar. 13, 2012; U.S. Pat. No.

8,066,641, entitled "Method and System for Photoaged Tissue," issued Nov. 29, 2011; U.S. Pat. No. 7,491,171, entitled "Method and System for Treating Acne and Sebaceous Glands," issued Feb. 17, 2009; U.S. Pat. No. 7,615,016, entitled "Method and System for Treating Stretch Marks," issued Nov. 10, 2009; and U.S. Pat. No. 7,530,356, entitled "Method and System for Noninvasive Mastopexy," issued May 12, 2009."

It is believed that the disclosure set forth above encompasses at least one distinct invention with independent utility. While the invention has been disclosed in the exemplary forms, the specific embodiments thereof as disclosed and illustrated herein are not to be considered in a limiting sense as numerous variations are possible. The subject matter of the inventions includes all novel and non-obvious combinations and sub combinations of the various elements, features, functions and/or propeliies disclosed herein.

Various embodiments and the examples described herein are exemplary and not intended to be limiting in describing the full scope of compositions and methods of this invention. Equivalent changes, modifications and variations of various embodiments, materials, compositions and methods may be made within the scope of the present invention, with substantially similar results.

The invention claimed is:

1. A method for treating a surface of skin with an ultrasound system, the method comprising:
   a) directing, using the ultrasound system coupled to the surface of skin, a first ultrasound energy into the surface of skin, thereby creating a first shaped conformal region of elevated temperature in the surface of skin; and
   b) simultaneous to step a), directing, using the ultrasound system coupled to the surface of skin, a second ultrasound energy into a subsurface of skin, thereby creating a second shaped conformal region of elevated temperature in the subsurface of skin,
   wherein the first shaped conformal region of elevated temperature and the second shaped conformal region of elevated temperature have different shapes, sizes, or orientations, or a combination thereof,
   wherein at least a portion of the second shaped conformal region of elevated temperature is below at least a portion of the first shaped conformal region of elevated temperature,
   wherein the first ultrasound energy creates a transitional biological effect on the surface of skin without causing cell death, without causing a scar, and without causing permanent damage to the surface of the skin,
   wherein the second ultrasound energy creates a thermal effect to the subsurface of the skin, and
   wherein step a), step b), or step a) and b) initiate a permanent biological effect to the subsurface of the skin.

2. The method according to claim 1, wherein step a), step b), or step a) and b) create an optically visible effect on the surface of the skin.

3. The method according to claim 1 wherein the transitional biological effect is one of erythema, edema, and a transitional coagulative point.

4. The method according to claim 2, wherein the optically visible effect on the surface of the skin can be at least one of increasing skin elasticity, reducing skin oiliness, reducing skin pore size, smoothing skin texture, reducing hyperpigmentation, treating and/or preventing acne, reducing a blemish, reducing an appearance of spider veins and/or rosacea, reducing an appearance of scars, reducing an appearance of stretch marks, rejuvenating skin, increasing collagen in subcutaneous tissue, tightening of sagging sink, rejuvenating photoaged skin, increasing a thickness of a dermal layer, reducing a wrinkle on the surface of the skin, generating new tissue in the subcutaneous tissue, and combinations thereof.

5. The method according to claim 1, wherein the permanent biological effect is at least one of stimulating or increase an amount of heat shock proteins, cause white blood cells to promote healing of tissue, accelerating a wound healing cascade in subcutaneous tissue, increasing blood perfusion in subcutaneous tissue, encouraging collagen growth, increasing liberation of cytokines, peaking inflammation, partially shrinking collagen, denaturing of proteins in the subcutaneous tissue, and combinations thereof.

6. The method according to claim 1 wherein the permanent biological effect is at least one of creating immediate or delayed cell death, collagen remodeling, disrupting or modifying of biochemical cascades, producing new collagen, stimulating cell growth, stimulating angiogenesis, stimulating a cell permeability response, enhancing delivery of medicants to tissue, and combinations thereof.

7. The method according to claim 1, the method further comprising administering a medicant to the surface and the subsurface of the skin.

8. The method according to claim 7, the method further comprising activating the medicant in at least one of the surface and the subsurface of the skin with a third ultrasound energy.

9. The method according to claim 1, the method further comprising delivering a secondary energy to the surface and the subsurface of the skin.

10. The method according to claim 9, wherein the secondary energy is a photon-based energy.

11. The method according to claim 2, wherein the optically visible effect to the surface of the skin is a cosmetic effect.

12. The method according to claim 1, wherein the first or second shaped conformal region of elevated temperature is created through an adjustment of spatial parameters of the first and/or second ultrasound energy, temporal parameters of the first and/or second ultrasound energy, or a combination of spatial and temporal parameters of the first and/or second ultrasound energy.

* * * * *